US008338488B2

(12) United States Patent
Pruss et al.

(10) Patent No.: US 8,338,488 B2
(45) Date of Patent: Dec. 25, 2012

(54) USE OF AT LEAST ONE OXIME DERIVATIVE OF 3,5-SECO-4-NOR-CHOLESTANE AS ANTIOXIDANTS

(75) Inventors: Rebecca Pruss, Cassis (FR); Cyrille Drouot, Draguignan (FR)

(73) Assignee: Trophos, Marseille Cedex (FR)

( * ) Notice: Subject to any disclaimer, the term of this patent is extended or adjusted under 35 U.S.C. 154(b) by 236 days.

(21) Appl. No.: 12/670,482

(22) PCT Filed: Jul. 24, 2008

(86) PCT No.: PCT/FR2008/001102
§ 371 (c)(1),
(2), (4) Date: Jun. 25, 2010

(87) PCT Pub. No.: WO2009/044011
PCT Pub. Date: Apr. 9, 2009

(65) Prior Publication Data
US 2010/0267837 A1 Oct. 21, 2010

(30) Foreign Application Priority Data

Jul. 25, 2007 (FR) ..................................... 07 05428

(51) Int. Cl.
*A61K 31/15* (2006.01)
*A61K 31/12* (2006.01)

(52) U.S. Cl. ........................................ 514/640; 514/675
(58) Field of Classification Search .................. 514/640, 514/675
See application file for complete search history.

(56) References Cited

U.S. PATENT DOCUMENTS 7,985,774 B2 * 7/2011 Pruss et al. .................... 514/640
2007/0237735 A1 10/2007 Denommee

FOREIGN PATENT DOCUMENTS

| FR | 2874923 | 3/2006 |
| FR | 2898272 | 9/2007 |
| GB | 546127 | 6/1942 |
| WO | 2007078452 | 7/2007 |

OTHER PUBLICATIONS

Krstic, et al., Synthesis of some steroidal oximes, lactams, thiolactams and their antitumor activities, 2007, pp. 406-414, vol. 72.

* cited by examiner

*Primary Examiner* — Raymond Henley, III
(74) *Attorney, Agent, or Firm* — Browdy and Neimark, P.L.L.C.

(57) ABSTRACT

The invention relates to the use of at least one oxime derivative of 3,5-seco-4-norcholestane as antioxidants in the cosmetics and food fields, and as antioxidant preservatives that can be used, in particular, in cosmetic, food and pharmaceutical products.

20 Claims, 1 Drawing Sheet

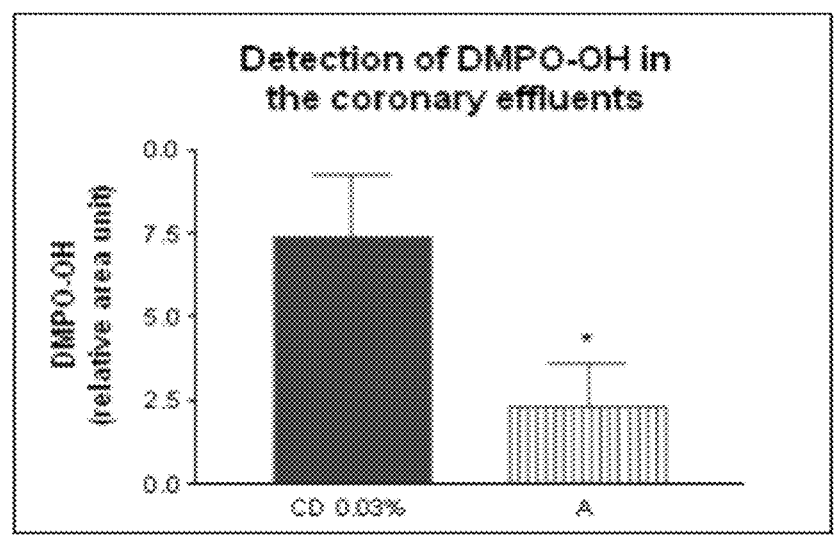

USE OF AT LEAST ONE OXIME DERIVATIVE OF 3,5-SECO-4-NOR-CHOLESTANE AS ANTIOXIDANTS

BACKGROUND OF THE INVENTION

The present invention relates to the use of at least one oxime derivative of 3,5-seco-4-nor-cholestane for its antioxidant property. More particularly, the present invention relates to the use of at least one oxime derivative of 3,5-seco-4-nor-cholestane as antioxidants in the cosmetics and food fields, and as an antioxidant preservative which can be used in particular in cosmetic, food, and pharmaceutical products.

Oxidative stress is one of the biological consequences of the use of oxygen by the organism. It leads to the formation of free radicals in the cells. Free radicals, if not controlled, can rapidly react with molecules surrounding them, giving rise to toxic compounds which can interfere with normal physiological processes. These substances can lead to cell damage if the antiradical defences are insufficient. More and more studies show that reactive oxygen species play an important role in multiple biological processes and in particular in the development of multiple human pathologies, and in ageing.

The cumulative effects of these reactions can overwhelm the normal cell repair mechanisms.

The role of cell oxidation in ageing and particularly cutaneous ageing, whether intrinsic or extrinsic, in particular light-induced, is known. Cutaneous ageing manifests itself by different clinical signs in particular the appearance of fine lines and deep wrinkles, increasing with age. Moreover, the appearance of the skin or the scalp deteriorates. The skin tone is generally altered and there may be diffuse irritations and sometimes telangiectasias on certain areas of the skin.

Another clinical sign of ageing is the dry and rough appearance of the skin which is essentially due to greater desquamation. Finally, a loss of firmness and tonicity of the skin is noted which, as with wrinkles and fine lines, is at least partly explained by a dermal and epidermal atrophy as well as a flattening of the formation. It is therefore noted that the clinical signs of cutaneous ageing result essentially from a dysfunction of the main biological mechanisms involved in the skin.

Preventing or treating cutaneous ageing, whether intrinsic or extrinsic, and the clinical signs described above, comes down to maintaining or improving the appearance of the skin or scalp.

Different antioxidants capable of preventing or treating cutaneous ageing are described in the state of the art.

Antioxidants are substances which neutralize the free radicals or their actions. Thus, they help to protect cells against the damage caused by free radicals.

The natural antioxidant molecules include for example vitamins (A, E and C in particular), carotenoids (such as beta-carotene), polyphenols, and trace elements (such as selenium, copper and zinc).

The beneficial effect of an exogenous supply of antioxidant to limit oxidative stress and reinforce the antioxidant defence, by ingestion, is known. Recent scientific data have shown that, in certain animal species, the administration of antioxidants effectively halts the ageing process and increases the animal's longevity.

It is thus sometimes beneficial, in order to allow the organism to function normally, to ingest components possessing an antioxidant action in a sufficient quantity.

Antioxidants also have a beneficial effect when applied to the skin, they are in fact used in cosmetics.

The use of antioxidants as preservatives, in various types of products sensitive to oxidation, is also known.

However, the compounds used as antioxidants are sometimes inappropriate or have an insufficient action. It is known for example that tocopherol which is a reference product in this field is sensitive to light and requires particular preservation means.

There is still therefore a real need for antioxidant compounds, and it would be useful to have new antioxidants having a powerful antioxidant activity which would have a beneficial effect in the cosmetics field, in the food field, and also an effect on the preservation of products.

SUMMARY OF THE INVENTION

The present invention is a response to this demand for powerful antioxidant compounds since it involves the use of at least one oxime derivative of 3,5-seco-4-nor-cholestane, which are powerful antioxidants, as an antioxidant.

In fact the inventors have now shown the powerful antioxidant role of at least one oxime derivative of 3,5-seco-4-nor-cholestane, and in particular 3,5-seco-4-nor-cholestane oxime vis-à-vis the peroxidation of lipids and also vis-à-vis substances capable of undergoing heat- or light-induced oxidation reactions (such as proteins, sugars, pigments, vitamins, polymers).

This is why a subject of the present invention is the use of at least one oxime derivative of 3,5-seco-4-nor-cholestane as an antioxidant.

According to the invention the term "antioxidant" refers to the ability of a compound to reduce the damage caused by free radicals:

in the organism, as an active ingredient in the cosmetics field and in the food field, and in any type of product requiring it as a preservative in order to be better preserved.

Any use of the compounds as active ingredients for a therapeutic application is excluded.

In addition to their excellent antioxidant properties, these compounds have the following advantages:

their synthesis can be carried out on the scale of several kilograms without industrial problem.

because they are powerful antioxidants, the necessary dose is very low;

these compounds do not absorb in the UV/visible region, they do not therefore interfere with conventional sun products which absorb UV rays and present no risk of chemical instability in this wavelength range;

these compounds are presented in the form of crystalline powder and can be stored very well at ambient temperature, with no degradation for at least 12 months;

they possess good solubility in fats;

they are colourless, tasteless and odourless, which is an advantage for use in the food and cosmetics fields in particular;

they are bioavailable, which makes them compounds which can be expected to have a systemic activity by oral route;

The antioxidant properties of the compounds of the invention make them suitable for use in the cosmetics field.

Thus, a first aspect of the invention is the use of at least one oxime derivative of 3,5-seco-4-nor-cholestane to protect the skin.

The skin is in particular the site of attack by extrinsic and intrinsic toxic factors. The extrinsic factors include for example ultraviolet radiation, wind, low humidity, abrasives and strong surfactants. The intrinsic factors include chronological ageing and biochemical changes in the skin.

A cause-effect relationship exists between repeated exposure to UV and premature ageing of the skin. Excessive exposure to the sun contributes to a premature reduction in the quality and quantity of elastin and collagen in the skin, and to hypertrophy of the epidermis. These changes are manifested by typical signs of ageing, such as wrinkles, a loss of elasticity, a dryness of the skin and a greater frequency of spots, and benign or malignant neoplasias.

The compounds of the present invention are capable of providing effective protection against the factors which cause the appearance of wrinkles and other histological changes associated with ageing of the skin.

It is therefore also one of the subjects of the invention to use the antioxidant properties of the compounds according to the invention on the symptoms of ageing due to UV, i.e. on the damage to the skin which appears as the result of repeated exposure to the sun in order to prevent, remove and treat wrinkles, fine lines of the skin, and/or combat cutaneous and/or subcutaneous relaxation; and/or improve the texture of the skin and revive the lustre of the skin; and/or reduce the size of the pores of the skin.

The useful properties of the compounds of the invention, their zero absorption in the UVA and UVB spectrum, also justify their use in a sun-protection cream, with no risk of interfering with the action of the components especially chosen for their UV absorption. The compounds of the invention are capable of trapping the form of oxygen activated by solar radiation. This activated form of oxygen, called singlet oxygen, is the reactive entity at the origin of cell disorders.

Another aspect of the invention consists of the use of the compounds of the invention in cleansing and/or make-up removal products, as well as in products for protection of the skin and/or hair against the side effects of UV.

The antioxidant properties of at least one oxime derivative of 3,5-seco-4-nor-cholestane also make them suitable for use in the food field in the form of a food supplement. It is therefore within the scope of the invention to use the compounds of the invention as antioxidants in the food field.

By antioxidant in the food field is meant in the present invention, a compound which, in the pure form or mixed with various supports and/or other permitted food additives, can be presented in powder form, in the form of gelatin capsules, tablets or other solid form which can optionally comprise a lipid, aqueous phase or be in oral solution or suspension.

Advantageously, the compound can be consumed alone, between meals, or during meals.

Advantageously, it can be consumed during meals, as a food supplement, combined with other foods. It is preferably incorporated in or sprinkled on a food. In practice the foods can be simple or mixed foods, and can be presented in all the usual forms known for human consumption. By food is meant within the meaning of the present invention, any food which can be ingested alone or accompanied, raw or cooked, prepared or not prepared, in any way whatever, such as for example meats and meat-based products, sea and freshwater products, milk and dairy products, including infant's milk, eggs and egg products, fruit and vegetables, cereals and cereal-based products, starchy products such as dough and rice, oils, vinegars and condiments, sauces and edible fats, sweetened products, jams, jellies, compotes, spreads, confectionary, preserves and semi-preserves, soups, coffee, tea, beverages, pastry, cocoa, chocolate, ices, meal replacements, ready-made and freshly prepared, quick-frozen or sterilized meals, bread and breadmaking products.

Thus, the compound can accompany any food without interfering with the taste and does not constitute a constraint for the consumer. Taking it can be seen as part of the food preparation process. It is not like taking medicaments or eating substitute meals. The compounds according to the invention can be frozen or, by contrast, heated without losing their properties.

The invention also relates to the use of the compounds according to the invention as antioxidant preservatives in different products, in particular cosmetic, food, and pharmaceutical products.

By preservative is meant a compound which keeps a product from any physico-chemical alteration.

It is known that fats and certain active substances used in cosmetic, dermatological, pharmaceutical, or detergent compositions in particular, have a tendency to oxidize, even at ambient temperature, and that this oxidation causes them to acquire new, in particular olfactory, properties which are undesirable. It is known for example that certain soaps develop rancid, spicy and fruity odours after only a few weeks of storage in the air. These unpleasant odours can be prevented or at least avoided for a much longer storage period if one of the compounds of the invention is added to them. Similar effects have been observed with shampoos or also shower or bath gels, cosmetic creams and lotions, cosmetic or skin or hair cleansing products containing substances which can oxidize in the air and/or in the light. It is within the scope of the invention to use the compounds of the invention as antioxidant agents for preserving cosmetic, dermatological, pharmaceutical, detergent and fragrance products.

Similarly, food products degrade under the action of oxidation in air, which causes changes in texture, colour and taste, and can make a food unfit for consumption.

The applicant has discovered that the compounds of the invention make it possible to ensure better preservation of the cosmetic or dermatological compositions comprising an oil phase, avoiding the rancidity of unsaturated lipids contained therein, and that they could also make it possible to avoid the oxidative degradation of active compounds contained in these compositions, such as vitamin A or the carotenoids.

It is therefore within the scope of this invention to use the compounds of the invention as preservatives, particularly for the preservation of the organoleptic and nutritional properties of foods and drinks, in particular fruit juices.

As the compounds according to the invention have high antioxidant capacities, they can be used as antioxidant preservatives of any lipid-based preparation including food, cosmetic, dermatological, fragrance, detergent products or pharmaceutical products.

A subject of the present invention is therefore the use of compounds according to the invention as preservatives, in particular in cosmetic or dermatological products, and food products.

This is why a subject of the present invention is the use of at least one oxime derivative of 3,5-seco-4-nor-cholestane or one of its addition salts with acceptable acids, or one of its esters or one of the addition salts of said esters with acceptable acids, as antioxidants.

Advantageously according to the invention at least one compound corresponding to formula I is used in which

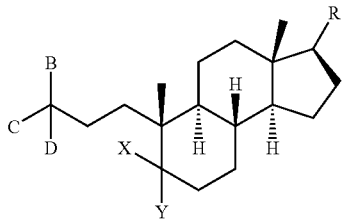

(I)

X and Y together represent an oxime group (=N—OH),

B represents a hydroxyl radical and C and D, identical or different, represent a hydrogen atom, or a linear or branched alkyl radical, comprising 1 to 4 carbon atoms, or B and C together represent a keto function and D a methyl, hydroxyl, or methylamine radical, or B and C represent a hydrogen atom and D a methylamine radical, or B and C together represent an oxime group and D a methyl radical, and R represents a linear or branched alkyl radical comprising 1 to 10 carbon atoms.

or one of its addition salts with pharmaceutically acceptable acids, or one of its esters or one of the addition salts with pharmaceutically acceptable acids of said esters, as an antioxidant.

The compounds of formula I as defined above are described in the international application published on 16th Mar. 2006 under number WO 2006/027454.

As understood by a person skilled in the art, a certain number of compounds of formula I which include one or more hydroxyl groups, can be esterified. These esters as well as their addition salts with pharmaceutically acceptable acids are not generally directly active in themselves but constitute prodrugs for the corresponding hydroxylated analogues. These esters, which are metabolized in the human organism, produce active compounds. These esters are also the subject of the present invention. There may be mentioned the esters introducing chemical functionalities such as sulphates, phosphates, acids and basic chains which increase aqueous solubility and bioavailability. The esters of compounds bearing a basic function are preferred, such as the dialkylglycine analogues with alkyls of 1 to 4 carbon atoms and quite particularly dimethylglycine and diethylglycine and also methylpiperazine. There may be mentioned fatty acid esters or polyethyleneglycol chain esters which increase affinity for the lipophilic phases. Saturated fatty acid chains with 3 to 18 carbon atoms are preferred.

In the present application and hereafter, the term "linear or branched alkyl radical with 1 to 4 carbon atoms" designates for example a methyl, ethyl, propyl, isopropyl radical preferably a methyl or ethyl radical and particularly a methyl radical.

The term "linear or branched alkyl radical with 1 to 10 carbon atoms>>designates for example a 2-methyl-3-ethyl heptane, 3-ethyl heptane, 3-methyl heptane radical, preferably a 2-ethyl heptane radical and particularly the 2-methyl heptane radical of cholestane, represented below

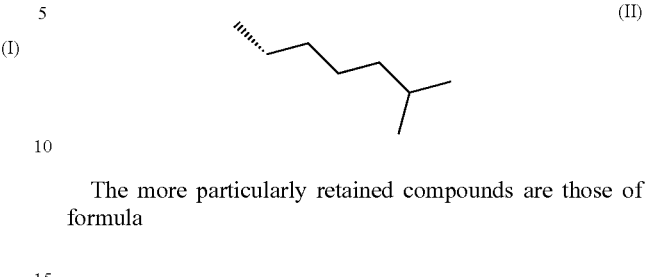

(II)

The more particularly retained compounds are those of formula

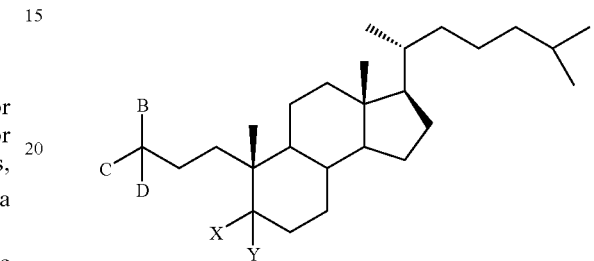

in which B, C, D, X and Y have the meaning already indicated.

Among the compounds of formula I described above, the compounds of formula I in particular are retained, for which X represents together with Y an oxime function as well as their esters and their addition salts with pharmaceutically acceptable acids.

The above compounds more particularly retained are those for which

B represents a hydroxyl radical and C and D represent a hydrogen atom, or C and D representing 2 linear or branched alkyl radicals with 1 to 4 carbon atoms, B represents together avec C a keto function and D represents a methyl, hydroxyl, methyl amine radical B represents a hydroxyl group, and C and D represent a hydrogen atom, or C and D represent 2 linear or branched alkyl radicals with 1 to 4 carbon atoms, or C represents a hydrogen atom and D a linear or branched alkyl radical with 1 to 4 carbon atoms, B and C represent a hydrogen atom and D a methyl amine group.

B together with C represent an oxime group, and D represents a methyl radical, as well as their esters and their addition salts with pharmaceutically acceptable acids.

The following are quite particularly retained:
3,5-seco-4-nor-cholestan-5-one oxime-3-ol,
3,5-seco-4-nor-cholestan-5-one oxime-3-methyl alcohol,
3,5-seco-4-nor-cholestan-5-one oxime-3-dimethyl alcohol, or one of their addition salts with pharmaceutically acceptable acids, or one of their esters or one of the addition salts with pharmaceutically acceptable acids of said esters.

According to the invention, the addition salts with pharmaceutically acceptable acids can be for example salts formed with hydrochloric, hydrobromic, nitric, sulphuric, phosphoric, acetic, formic, propionic, benzoic, maleic, fumaric, succinic, tartaric, citric, oxalic, glyoxylic, aspartic or alkane sulphonic acid such as methane or ethane sulphonic, or arylsulphonic acid, such as benzene or paratoluene sulphonic, or carboxylic acids.

It is understood according to the invention that the oxime group represents the two syn and anti isomers in a mixture or isolated.

Of course according to the invention it is possible to use the oxime derivative of 3,5-seco-4-nor-cholestane alone or in a mixture with at least one other oxime derivative of 3,5-seco-4-nor-cholestane.

It is also possible to use the oxime derivatives of 3,5-seco-4-nor-cholestane alone or in a mixture as described previously in combination with one or more other compounds known for their antioxidant properties.

There may be mentioned as examples of other compounds known for their antioxidant properties, the compounds originating from the families of the thiols and the phenols and polyphenols such as for example flavonoids (very widespread in vegetables), phenolic acids (in cereals, fruits and vegetables), tannins (in cocoa, coffee, tea, grapes, etc.), anthocyans (in particular in red fruits; β-carotene (provitamins A); the tocopherols (vitamin E) or its esters such as alpha-tocopherol, gamma-tocopherol, delta-tocopherol; certain metal chelating agents or ascorbic acid and its esters such as sodium or calcium ascorbate; diacetyl 5-6-1-ascorbic acid, palmityl 6-1-ascorbic acid, citric acid and citrates such as sodium, potassium and calcium citrates; tartaric acid and tartrates such as sodium and potassium tartrates; butylhydroxyanisol and butylhydroxytoluol; octyl or dodecyl gallates; sodium, potassium or calcium lactates; lecithins; glutathione, or enzymes such as catalase, the superoxide dismutases and certain peroxidases.

The antioxidants which can be used in the composition of the invention can be natural or synthetic.

Thus, one of the aspects of the invention is therefore to propose an antioxidant cosmetic composition comprising in a cosmetically acceptable medium at least an effective quantity of at least one oxime derivative of 3,5-seco-4-nor-cholestane.

A subject of the invention is also a cosmetic composition intended to combat chronobiological and/or light-induced ageing comprising, in a cosmetically acceptable medium, an effective quantity of at least one oxime derivative of 3,5-seco-4-nor-cholestane.

By cosmetically acceptable medium is meant compatible with the skin, scalp, mucous membranes, nails and hair.

The quantity of oxime derivative of 3,5-seco-4-nor-cholestane or of one of its derivatives which can be used according to the invention obviously depends on the sought effect and must be in an effective quantity in order to produce the sought antioxidant effect.

By way of example the quantity of at least one oxime derivative of 3,5-seco-4-nor-cholestane or of its derivatives which can be used according to the invention can range for example from 0.01% to 30% and preferably from 0.1% to 10% of the total weight of the composition.

The composition according to the invention obviously comprises a cosmetically acceptable support and can be presented in all the galenic forms normally used, particularly for a topical application. Thus the composition can be presented in particular in the form of an aqueous, hydroalcoholic or oily solution, an oil-in-water or water-in-oil or multiple emulsion, an aqueous or oily gel, an anhydrous liquid, pasty or solid product, a dispersion of oil in an aqueous phase using spherical particles, which spherical particles can be polymeric nanoparticles such as nanospheres and nanocapsules or, better, ionic and/or non-ionic type lipid vesicles.

This composition can be more or less fluid and have the appearance of a white or coloured cream, an ointment, milk, lotion, serum, paste or foam. It can optionally be applied to the skin in the form of an aerosol. It can also be presented in solid form, and for example in stick form.

The composition of the invention can be used as a care product, as a cleansing product, as a make-up product or also as a simple deodorant product.

In a known manner, the composition of the invention can also contain the usual adjuvants in the cosmetics and dermatological fields, such as hydrophilic or lipophilic gelling agents, hydrophilic or lipophilic active ingredients, preservatives, solvents, fragrances, fillers, filters, pigments, chelating agents, odour absorbers and colorants. The quantities of these different adjuvants are those used in a standard fashion in the fields considered, and for example from 0.01% to 20% of the total weight of the composition. These adjuvants, according to their nature, can be introduced into the oil phase, the aqueous phase, lipid vesicles and/or nanoparticles.

When the composition of the invention is an emulsion, the proportion of the oil phase can range from 5% to 80% by weight, and preferably from 5% to 50% of the total weight of the composition. The oils, the emulsifying agents and the coemulsifying agents used in the composition in the form of emulsion are chosen from those used in a standard fashion in the field considered. The emulsifying agent and the coemulsifying agent are present, in the composition, in a proportion ranging from 0.3% to 30% by weight, and preferably from 0.5% to 20% of the total weight of the composition.

As oils which can be used in the invention, there may be mentioned mineral oils, oils of vegetable origin (apricot oil, sunflower oil, shea butter), oils of animal origin, synthetic oils, silicone oils and fluorinated oils (perfluoropolyethers). It is also possible use as fats fatty alcohols (cetyl alcohol), fatty acids, waxes (beeswax).

As emulsifying agents and coemulsifying agents which can be used in the invention, there may be mentioned for example fatty acid and polyethylene glycol esters such as PEG-40 stearate, PEG-100 stearate, fatty acid and polyol esters such as glyceryl stearate and sorbitan tristearate.

As hydrophilic gelling agents, there may be mentioned in particular the carboxyvinyl polymers (carbomers), acrylic copolymers such as the acrylate/alkylacrylate copolymers, the polyacrylamides, the polysaccharides, natural gums and clays, and, as lipophilic gelling agents, there may be mentioned modified clays such as the bentones, metal salts of fatty acids, hydrophobic silica and the polyethylenes.

The composition can contain other hydrophilic active ingredients such as proteins or protein hydrolysates, amino acids, polyols, urea, allantoin, sugars and sugar derivatives, water-soluble vitamins, vegetable extracts and hydroxy acids.

As lipophilic active ingredients, it is possible to use retinol (vitamin A) and derivatives thereof, tocopherol (vitamin E) and derivatives thereof, essential fatty acids, ceramides, essential oils, salicylic acid and derivatives thereof.

It is also possible to use, according to the invention, in combination with at least one oxime derivative of 3,5-seco-4-nor-cholestane, compounds chosen from:
  vegetable hormones (auxins);
  antibacterial agents such as the macrolides, pyranosides and tetracyclines, and in particular erythromycin;
  calcium antagonists, such as verapamil and diltiazem;
  OH radical scavengers, such as dimethyl sulphoxide;
  vegetable extracts such as those of Iridaceae or soya, extracts which may or may not contain isoflavones;
  extracts of micro-organisms including in particular bacterial extracts such as those of non-photosynthetic filamentous bacteria.

Other compounds can also be added to the above list, namely for example potassium channel openers such as diazoxide and minoxidil, spiroxazone, phospholipids such as lecithin, linoleic and linolenic acids, salicylic acid and derivatives thereof described in the French patent FR 2 581 542, such as the salicylic acid derivatives bearing an alkanoyl group having 2 to 12 carbon atoms in position 5 of the benzene ring, hydroxycarboxylic or ketocarboxylic acids and its esters, lactones and their corresponding salts, anthralin, carotenoids, eicosatetraenoic and eicosatrienoic acids or esters and amides thereof, vitamin D and derivatives thereof.

According to the invention, it is possible, inter alia, to combine the oxime derivative of 3,5-seco-4-nor-cholestane or of one of its derivatives with other active ingredients intended in particular for the prevention and/or treatment of cutaneous diseases. Among these active ingredients, there may be mentioned by way of example:

- agents modifying cutaneous differentiation and/or proliferation and/or pigmentation such as retinoic acid and its isomers, retinol and its esters, vitamin D and derivatives thereof, oestrogens such as oestradiol, kojic acid or hydroquinone;
- agents modifying bacterial adhesion to the skin and/or mucous membranes such as honey, in particular acacia honey and certain sugar derivatives;
- antiparasitics, in particular metronidazole, crotamiton or pyrethrinoids;
- antifungals, especially compounds belonging to the imidazole class, such as econazole, ketoconazole or miconazole or salts thereof, polyene compounds such as amphotericin B, compounds of the allylamine family such as terbinafine, or also octopirox.
- antiviral agents such as acyclovir;
- steroidal anti-inflammatory agents such as hydrocortisone, betamethasone valerate or clobetasol propionate, or nonsteroidal anti-inflammatory agents such as ibuprofen and salts thereof, diclofenac and salts thereof, acetylsalicylic acid, paracetamol or glycyrrhetinic acid;
- anaesthetic agents such as lidocaine hydrochloride and derivatives thereof;
- antipruritic agents such as thenaldine, trimeprazine or cyproheptadine;
- keratolytic agents such as alpha- and beta-hydroxycarboxylic or beta-ketocarboxylic acids, salts, amides or esters thereof, and more particularly hydroxy acids such as glycolic acid, lactic acid, malic acid, salicylic acid, citric acid and the fruit acids in general, and 5-n-octanoylsalicylic acid;
- antiseborrhoeics such as progesterone;
- antidandruff agents such as octopirox or zinc pyrithione;
- anti-acne agents such as retinoic acid or benzoyl peroxide.
- substances such as substance P antagonists, CGRP antagonists or bradykinin antagonists or NO synthase inhibitors, compounds described as being active in the treatment of sensitive skins and as having anti-irritant effects, in particular vis-à-vis irritant compounds which may be present in the compositions.

Thus, another subject of the invention relates to a composition comprising an effective quantity of at least one 3,5-seco-4-nor-cholestane oxime and at least one agent chosen from the antibacterial, antiparasitic, antifungal, antiviral, anti-inflammatory, antipruritic, anaesthetic, keratolytic, antiseborrhoeic, antidandruff, anti-acne agents, agents modifying cutaneous differentiation and/or proliferation and/or pigmentation, substance P antagonists, CGRP antagonists or bradykinin antagonists or NO synthase inhibitors.

As active ingredients, it is possible to use in particular moisturizers such as polyols (for example glycerine), vitamins (for example D-panthenol), anti-inflammatory agents, soothing agents (allantoin, cornflower water), UVA and UVB filters, mattifying agents (for example the partially crosslinked polydimethylorganosiloxanes sold under the name KSG® by Shin Etsu), and mixtures thereof.

Antiwrinkle active ingredients can also be added, in particular tensor products such as vegetable proteins and their hydrolysates, in particular the soya protein extract sold under the name Eleseryl® by LSN or the oat derivative sold under the name Reductine® by Silab.

Other characteristics and advantages of the invention will become clearer from the following examples and attached FIG. 1, given by way of a non-limitative illustration. In what follows, or in the above, the proportions are given in percentage by weight, unless otherwise indicated.

BRIEF DESCRIPTION OF THE DRAWINGS

FIG. 1 shows the quantification of the DMPO-OH scavenging adducts of the hydroxyl radical on DMPO nitrone (50 mM) detected in the coronary effluents of ischemic hearts after 3 minutes of reperfusion.

DETAILED DESCRIPTION OF THE INVENTION

The following examples illustrate the present application without however limiting it.

EXAMPLE 1

Competition of 3,5-seco-4-nor-cholestan-5-one oxime-3-ol with 5,5-dimethyl-1-pyrroline-1-oxide in the Presence of Free Radicals The antiradical properties of the claimed products are demonstrated by carrying out a competition study with a reference product belonging to the nitrone family. The nitrones such as DMPO (5,5-dimethyl-1-pyrroline-1-oxide) are broadly described as being compounds exhibiting very high reactivity vis-à-vis the free radicals (Novelli G. P. et al. Free Radical Res. Commun. 1986.1, 321). The nitrones trap the radical species (R.; RO.) and allow their observation by electron paramagnetic resonance (EPR) (Degray J. et al. Electron Spin Resonance, Ed N. M. Atherton, Atheaeum Press Ltd; Cambridge, 1994, 14, 246).

The incubation of the DMPO (Interchim-U2469) (20 mM) in deoxygenated toluene (Sigma-Aldrich) in the presence of the tBuO (tert-butoxyl) radical, generated by photolysis, makes it possible to identify and quantify by EPR the signal of the DMPO-tBuO radical. This signal is inhibited in the presence of an equimolar quantity of 3,5-seco-4-nor-cholestane oxime.

The EPR signal allows integration in the form of an area of the signal of the DMPO-tBuO adduct and therefore a relative quantification of this radical entity.

All the experiments were carried out on an X-band Bruker ESP300 device (9.5 GHz) at ambient temperature. The solutions were studied in a quartz EPR tube.

The data are presented as figures in the table below.

| t-BuO.: (t-BuO)$_2$ 20 mM photolysis at 350 nm | Area of the DMPO-tBuO signal at 200 s in relative units | Area of the DMPO-tBuO signal at 400 s in relative units |
|---|---|---|
| DMPO (20 mM) alone | 6.0 | 9 |
| DMPO (20 mM) + 3,5-seco- | 3 | 4 |

| t-BuO.: (t-BuO)$_2$ 20 mM photolysis at 350 nm | Area of the DMPO-tBuO signal at 200 s in relative units | Area of the DMPO-tBuO signal at 400 s in relative units |
|---|---|---|
| 4-nor-cholestan-5-one oxime-3-ol (20 mM) % inhibition of the DMPO-tBuO radical | 50% | 66% |

Conclusion

The 3,5-seco-4-nor-cholestan-5-one oxime-3-ol inhibits of the order of 60% of the level of the DMPO-tBuO signal radical with rapid kinetics, less than 10 minutes. The intensity of the scavenging of the tBuO radical and its kinetics demonstrate the anti-radical and therefore antioxidant property of the claimed compounds.

EXAMPLE 2

Antioxidant Effect of 3,5-seco-4-nor-cholestan-5-one oxime-3-ol in the Model of Oxidation of Cumene by Activated Oxygen In order to demonstrate the relevance of the antioxidant effect of 3,5-seco-4-nor-cholestan-5-one oxime-3-ol, the inhibition of the oxidation of the cumene in hydroperoxy-cumene was studied. This test shows the benefit of involving the biologically most relevant oxidant, i.e. gaseous oxygen. The oxidation of cumene at atmospheric pressure and at 37° C. by oxygen is known and described in the presence of a radical initiator such as AIBN (azobisisobutyronitrile) (Blanchard H. S., J. Am. Chem. Soc. 1959, 81, 4548). A recent publication used this reaction to classify the antioxidant potential of known products such as vitamin E (which is the universal reference), BHT (butylated hydroxytoluene) and other products.

In the following experiment we reproduced the same experimental conditions as those described in the publication of Becker D. A. et al. (J. Am. Chem. Soc. 2002, 124, 4678-4684). A high pressure liquid chromatography method coupled with a UV detector was used to detect cumene hydroperoxide. The column used is an Agilent Zorbax Eclipse XDB RPC8 column (150×4.6 mm) coupled with a UV detector fixed at 254 nm. The gradient used is detailed in the following table:

| Time (min) | % water | % Acetonitrile | Flow rate ml/min |
|---|---|---|---|
| 0 | 35 | 65 | 1.5 |
| 5 | 35 | 65 | 1.5 |
| 5.5 | 0 | 100 | 1.5 |
| 10 | 0 | 100 | 1.5 |

Experimental Conditions:

2 ml of cumene (AcrosOrganic) and 0.5 ml of methanol are mixed, azobisisobutyronitrile (AcrosOrganic) is added (2 equivalents) and the solution taken to 45° C. in order to accelerate the chemical reaction. The cumene hydroperoxide appears over time and is assayed by the HPLC method. A straight line of linear regression is established in order to demonstrate that the quantification of the appearance of cumene hydroperoxide is possible. The results are shown in the following table:

| Cumene hydroperoxide concentration (mM) | Time (min) |
|---|---|
| 0.25 | 0 |
| 1 | 15 |
| 1.5 | 30 |
| 2.2 | 45 |
| 3 | 60 |
| 3.7 | 75 |

The straight line of linear regression obtained corresponds to the following formula: y=0.0444x+0.2694 with $R^2$=0.994

The technique used made it possible to compare the appearance of the cumene hydroperoxide in the presence of an antioxidant agent such as the claimed products and vitamin E used as reference product.

The experimental data and the results in percentages of the oxidation of the cumene are presented in the table below.

| Experimental conditions: | Incubation | Area of the signal, in relative units, of the cumene hydroperoxide | % of reduction of the oxidation of the cumene |
|---|---|---|---|
| Cumene - Methanol + 50 µM of 3,5-seco-4-nor-cholestan-5-one oxime-3-ol and 2 equivalents of AIBN | 2 hours 45° C. | 300 | 25% |
| Cumene - Methanol + 200 µM of 3,5-seco-4-nor-cholestan-5-one oxime-3-ol and 2 equivalents of AIBN | 2 hours 45° C. | 200 | 50% |
| Cumene - Methanol + 100 µM of vitamin E and 2 equivalents of AIBN | 2 hours 45° C. | 245 | 39% |
| Cumene - Methanol and 2 equivalents of AIBN | 2 hours 45° C. | 400 | 0% (positive control) |

In conclusion the 3,5-seco-4-nor-cholestan-5-one oxime-3-ol reduces by approximately 40% the oxidation of the cumene by oxygen and exhibits an activity of the same order of magnitude vis-à-vis vitamin E under these conditions at the same concentrations.

EXAMPLE 3

Study of Pharmacokinetics in the Rat with 3,5-seco-4-nor-cholestan-5-one oxime-3-ol A study of pharmacokinetics with administration by oral route in suspension in corn oil and by intra-venous route in solution in cremophor/ethanol/water (5%, 10%, 85%) made it possible to calculate the bioavailability of the product. The assay of the product in the plasma is carried out by a high pressure liquid chromatography method coupled with mass spectrometry.

Thus, at a dose of 500 mg/kg administered by oral route, the bioavailability was calculated at 6%. The circulating level of 3,5-seco-4-nor-cholestan-5-one oxime-3-ol oxime is therefore quantifiable and demonstrates a real absorption of the product.

EXAMPLE 4

Chemical Stability of 3,5-seco-4-nor-cholestan-5-one oxime-3-ol

A study of chemical stability under the storage conditions described in the ICH standards (International Conference on Harmonization of Technical Requirements for Registration of Pharmaceuticals for Human Use) for the product stored in the state of powder demonstrated very high chemical stability. These analyses were carried out using a gas chromatography method coupled with an FID detector. This method makes it possible to quantify the impurities at a level of 0.2%. The results (total impurities at each time) are shown in the following table.

| Storage conditions | T0 | T6 months | T12 months |
| --- | --- | --- | --- |
| 25° C. under 60% relative humidity | 0.2% | — | 0.2% |
| 40° C. under 75'"% relative humidity | 0.2% | 0.2% | — |

No change in the quality of the product is demonstrated after 6 months of storage at 40° C. and after 1 year's storage at 25° C.

EXAMPLE 5

Antioxidant Activity of 3,5-seco-4-nor-cholestan-5-one oxime-3-ol (A) on a Perfused Isolated Rat Heart Experimental Model The animals used are male rats of the Sprague Dawley strain (Harlan et CERJ, France) of 250-300 g) fed ad libitum. The rats are anaesthetized by an intraperitoneal injection of sodium pentobarbital (50 mg/kg of body weight). The thoracic cavity is then opened and the heart rapidly removed and immersed in perfusion liquid (Krebs-Henseleit) at 4° C. in order to stop any contraction.

The heart with fatty tissues removed is then perfused according to Langendorff's technique by aortic retrograde route at a constant pressure of 90 cm $H_2O$. A small incision in the pulmonary artery allows the flow and measurement of the coronary effluent over time (coronary flow rate). The time required for completion of the entire operation is two to three minutes. After ablation of the left auricle, a latex cuff is inserted into the left ventricle and filled with a volume of distilled water (50-60 μl) which remains constant during the experimental protocol, connected to a pressure sensor (GOULD) and to a differentiating recorder allowing the measurement of the following haemodynamic parameters:

- intraventricular diastolic pressure (Pdia)
- developed pressure of left ventricle Pdev=Psystolic−Pdia
- dP/dt (first derivative of the developed pressure, cardiac contractility index in this model)
- cardiac frequency (F)
- cardiac work calculated according to the relationship W=Pdev×F The coronary flow rate as well as all of the haemodynamic parameters are measured every 5 minutes.

The perfusion medium is a buffered Krebs-Henseleit ionic solution of pH 7.35, saturated with a gaseous mixture (95% $O_2$/5% $CO_2$), containing NaCl (119 mM), $NaHCO_3$ (25 mM), KCl (5.9 mM), $MgSO_4$ (1.2 mM) EDTA (0.5 mM), glucose (11 mM, heart substrate) and $CaCl_2$ (2.5 mM). The compound 3,5-seco-4-nor-cholestan-5-one oxime-3-ol (A) is diluted in this Krebs buffer at 1 μM of 3,5-seco-4-nor-cholestan-5-one oxime-3-ol (A) starting from a 1000× solution in 30% hydroxylpropyl beta cyclodextrine in PBS. The control Krebs medium is prepared starting from a 1000× solution in 30% hydroxylpropyl beta cyclodextrine in PBS without the compound 3,5-seco-4-nor-cholestan-5-one oxime-3-ol (A) (CD 0.03%).

The perfused rats' hearts were subjected to the following protocol:
- an initial 30-minute equilibration period (CTR)
- ischaemia at a reduced flow rate (30% of the control coronary flow rate) for 10 minutes (RFI)
- total ischemia for 30 minutes (TI) at 37° C.
- reperfusion for 60 minutes (REP).

All the compounds or mixtures tested were perfused starting from the twentieth minute of CTR, all of the RFI. They were maintained in TI at 37° C., thus constituting an "incubation" liquid for the ischaemic myocardium, and were then again perfused throughout the reperfusion.

For the EPR experiments by scavenging of free radicals, the hearts were perfused according to the same protocol as the hearts previously described during the periods of control and ischaemia.

The DMPO nitrone (50 mM) is perfused as from the start of the reperfusion at the inlet to the aorta so as to scavenge the free radicals produced in the coronary effluents.

These effluents were collected by direct sampling from the coronary sinus at 3 minutes of reperfusion then preserved in liquid nitrogen before analysis by EPR of the adducts formed on this nitrone.

DMPO Spin Trapping in the Coronary Effluents

The EPR signals characteristic of the DMPO-OH adduct are detected in the effluents at the thirtieth minute of reperfusion in the presence of DMPO (50 mM).

With the perfusion of the compound 3,5-seco-4-nor-cholestan-5-one oxime-3-ol (A), a large and significant reduction ($p<0.05$) of the extracellular production of free radical scavenging adducts formed in the myocardium and captured on the DMPO is noted. These adducts are sufficiently persistent to be detected by EPR.

Statistical analyse of the results obtained on two groups of 6 hearts shows that perfusion with the compound 3,5-seco-4-nor-cholestan-5-one oxime-3-ol (A) 1 μM provides significant protection with respect to the vehicle (FIG. 1).

In conclusion, the compound 3,5-seco-4-nor-cholestan-5-one oxime-3-ol (A) reduces the release of the oxygenated radical species.

The invention claimed is:

1. A method for treating damage caused by oxidative free radicals, said method comprising administering to a subject in need thereof an effective amount of at least one antioxidant compound chosen from: an one oxime derivative of 3,5-seco-4-nor-cholestane, or an addition salt thereof with acceptable acids, or an ester thereof, or addition salt of said ester with acceptable acids.

2. The method of claim 1, wherein said oxime derivative of 3,5-seco-4-nor-cholestane comprises a compound of the following:

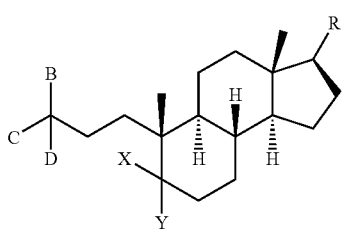

(I)

in which
X and Y together represent an oxime radical (=NOH), or X represents a hydroxyl and Y a hydrogen atom;
B represents a hydroxyl radical, and C and D are identical or different and represent a hydrogen atom, or a linear or branched alkyl radical comprising 1 to 4 carbon atoms;
or
B and C together represent a keto function, and D is a methyl, hydroxyl, or methylamine radical;
or
B and C represent a hydrogen atom, and D is a methylamine radical;
or
B and C together represent an oxime group, and D a methyl radical;
and
R represents a linear or branched alkyl radical comprising 1 to 10 carbon atoms.

3. The method of claim 2, wherein the linear or branched alkyl radical of 1 to 4 carbon atoms is a methyl, an ethyl, a propyl, or an isopropyl radical.

4. The method of claim 1, wherein the oxime derivative of 3,5-seco-4-nor-cholestane is chosen from compounds for which:
B represents a hydroxyl radical, and C and D represent a hydrogen atom, or C and D represent 2 linear or branched alkyl radicals of 1 to 4 carbon atoms;
or
B represents together with C a keto function, and D represents a methyl, a hydroxyl, or a methyl amine radical;
or
B represents a hydroxyl group, and C and D represent a hydrogen atom, or C and D represent 2 linear or branched alkyl radicals of 1 to 4 carbon atoms, or C represents a hydrogen atom and D is a linear or branched alkyl radical of 1 to 4 carbon atoms;
or
B and C represent a hydrogen atom, and D is a methyl amine group;
or
B together with C represent an oxime group, and D represents a methyl radical.

5. The method of claim 2, wherein the linear or branched alkyl radical of 1 to 10 carbon atoms is chosen from a 2-methyl-3-ethyl heptane radical, a 3-ethyl heptane radical, a 3-methyl heptane radical, a 2-ethyl heptane radical, or a 2-methyl heptane radical of the cholestane of the following formula (II)

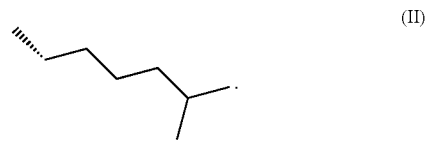

(II)

6. The method of claim 2, wherein the compound of formula I has the following formula III:

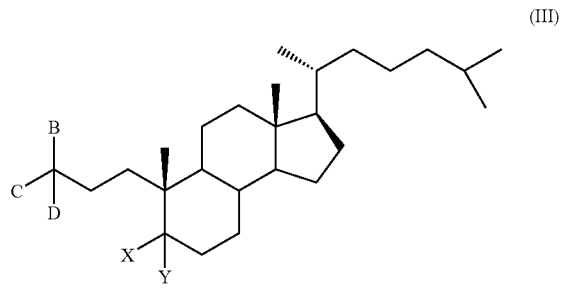

(III)

in which
X and Y together represent an oxime radical (=NOH), or X represents a hydroxyl and Y a hydrogen atom;
B represents a hydroxyl radical, and C and D are identical or different and represent a hydrogen atom, or a linear or branched alkyl radical comprising 1 to 4 carbon atoms;
or
B and C together represent a keto function, and D is a methyl, hydroxyl, or methylamine radical;
or
B and C represent a hydrogen atom, and D is a methylamine radical;
or
B and C together represent an oxime group, and D a methyl radical;
and
R represents a linear or branched alkyl radical comprising 1 to 10 carbon atoms.

7. The method of claim 1, wherein the oxime derivative of 3,5-seco-4-nor-cholestane is chosen from compounds in which X represents together with Y an oxime function.

8. The method of claim 1, wherein the oxime derivative of 3,5-seco-4-nor-cholestane is chosen from:
3,5-seco-4-nor-cholestan-5-one oxime- 3-ol,
3,5-seco-4-nor-cholestan-5-one oxime-3-methyl alcohol, or
3,5-seco-4-nor-cholestan-5-one oxime-3-dimethyl alcohol.

9. The method of claim 1, wherein the at least one antioxidant compound is administered in a cosmetic.

10. The method of claim 9, to combat oxidative stress.

11. The method of claim 9, to treat ageing, and/or cutaneous ageing.

12. The method of claim 11, for treating fine lines and deep wrinkles, modifications of the skin tone, dry and rough appearance of the skin, loss of firmness and/or tonicity of the skin.

13. The method of claim 1, wherein the at least one antioxidant compound is administered in a food.

14. The method of claim 13, wherein the at least one antioxidant compound is a food supplement.

15. The method of claim 1, wherein the at least one antioxidant compound is an antioxidant preservative, in cosmetic, food or pharmaceutical product.

16. The method of claim 1, wherein the oxime derivatives of 3,5-seco-4-nor-cholestane are used alone or in a mixture, optionally in combination with one or more other antioxidant compounds.

17. The method of claim 3, wherein the linear or branched alkyl radical of 1 to 4 carbon atoms is a methyl radical or an ethyl radical.

18. The method of claim 17, wherein the linear or branched alkyl radical of 1 to 4 carbon atoms is a methyl radical.

19. A method for preserving a cosmetic, pharmaceutical, or food product, said method comprising administering to said product an effective amount of at least one antioxidant compound chosen from: a one oxime derivative of 3,5-seco-4-nor-cholestane, or an addition salt thereof with acceptable acids, or an ester thereof, or addition salt of said ester with acceptable acids.

20. A method of reducing the production or release of oxidative free radicals in a subject, which comprises administering to said subject an effective amount of at least one antioxidant compound chosen from: a one oxime derivative of 3,5-seco-4-nor-cholestane, or an addition salt thereof with acceptable acids, or an ester thereof, or addition salt of said ester with acceptable acids.

* * * * *